US008945102B2

(12) United States Patent
Durrie et al.

(10) Patent No.: US 8,945,102 B2
(45) Date of Patent: Feb. 3, 2015

(54) LASER CORNEAL FLAP CUTTING SYSTEM AND ASSOCIATED METHODS

(75) Inventors: Daniel S. Durrie, Mission Hills, KS (US); George H. Pettit, Maitland, FL (US); John A. Campin, Orlando, FL (US)

(73) Assignee: Alcon Refractivehorizons, Inc. (CH)

( * ) Notice: Subject to any disclaimer, the term of this patent is extended or adjusted under 35 U.S.C. 154(b) by 2367 days.

(21) Appl. No.: 11/491,636

(22) Filed: Jul. 24, 2006

(65) Prior Publication Data

US 2007/0027439 A1 Feb. 1, 2007

Related U.S. Application Data

(60) Provisional application No. 60/703,671, filed on Jul. 29, 2005.

(51) Int. Cl.
*A61B 18/20* (2006.01)
*A61B 19/00* (2006.01)
*A61F 9/008* (2006.01)

(52) U.S. Cl.
CPC ............. *A61F 9/008* (2013.01); *A61F 9/00806* (2013.01); *A61F 9/00836* (2013.01); *A61F 2009/00846* (2013.01); *A61F 2009/00872* (2013.01); *A61F 2009/0088* (2013.01)
USPC .......... 606/5; 606/4; 606/10; 606/12; 128/898

(58) Field of Classification Search
CPC ................... A61F 2009/007; A61F 2009/008; A61F 2009/00844; A61F 2009/00848; A61F 2009/00878; A61F 2009/0088; A61F 2009/00882; A61F 9/007; A61F 9/008; A61F 9/00804

USPC ................ 606/4–6, 10–12, 107, 16; 128/898
See application file for complete search history.

(56) References Cited

U.S. PATENT DOCUMENTS

| | | | |
|---|---|---|---|
| 6,210,399 B1 * | 4/2001 | Parel et al. ......................... 606/5 |
| 6,299,309 B1 * | 10/2001 | Ruiz ............................. 351/212 |
| 6,908,196 B2 * | 6/2005 | Herekar et al. ............... 351/221 |
| 7,226,443 B1 * | 6/2007 | Campin et al. .................... 606/5 |
| 7,237,898 B1 * | 7/2007 | Hohla et al. ................. 351/246 |
| 2002/0052615 A1 * | 5/2002 | Ross et al. ..................... 606/166 |

(Continued)

OTHER PUBLICATIONS

Touboul D, Salin F, Mortemousque B, Chabassier P, Mottay E, Léger F, Colin J.,Advantages and disadvantages of the femtosecond laser microkeratome,J Fr Ophtalmol. May 2005;28(5):535-46.*

*Primary Examiner* — Ahmed Farah

(57) ABSTRACT

A method for performing wavefront-guided laser surgery on a cornea includes the step of calculating a corneal flap configuration based upon collected anatomical information on an eye and wavefront data on a cornea of the eye. Such data may be collected by, for example, an aberrometer, although this is not intended as a limitation. The calculated configuration is transmitted to a processor in controlling relation to a corneal flap-cutting device. The flap-cutting device is used to create a corneal flap based upon the calculated configuration. A system for performing wavefront-guided laser surgery on a cornea includes a processor for receiving the anatomical information and wavefront data. A software package is adapted to calculate the corneal flap configuration and to control a corneal flap-cutting device to cut a corneal flap commensurate with the calculated corneal flap configuration.

10 Claims, 2 Drawing Sheets

(56) References Cited

U.S. PATENT DOCUMENTS

| | | |
|---|---|---|
| 2002/0082629 A1* | 6/2002 | Cox et al. .................. 606/166 |
| 2002/0111607 A1* | 8/2002 | Bille ............................ 606/5 |
| 2003/0100893 A1* | 5/2003 | Bille ............................ 606/4 |
| 2003/0208190 A1* | 11/2003 | Roberts et al. ............... 606/5 |
| 2004/0054358 A1* | 3/2004 | Cox et al. .................... 606/5 |
| 2004/0116910 A1* | 6/2004 | Markman ..................... 606/5 |
| 2005/0096640 A1* | 5/2005 | Dai et al. .................... 606/10 |
| 2005/0187540 A1* | 8/2005 | Mrochen et al. ............. 606/5 |
| 2006/0173445 A1* | 8/2006 | Bille ............................ 606/5 |
| 2007/0161972 A1* | 7/2007 | Felberg et al. ............... 606/4 |

* cited by examiner

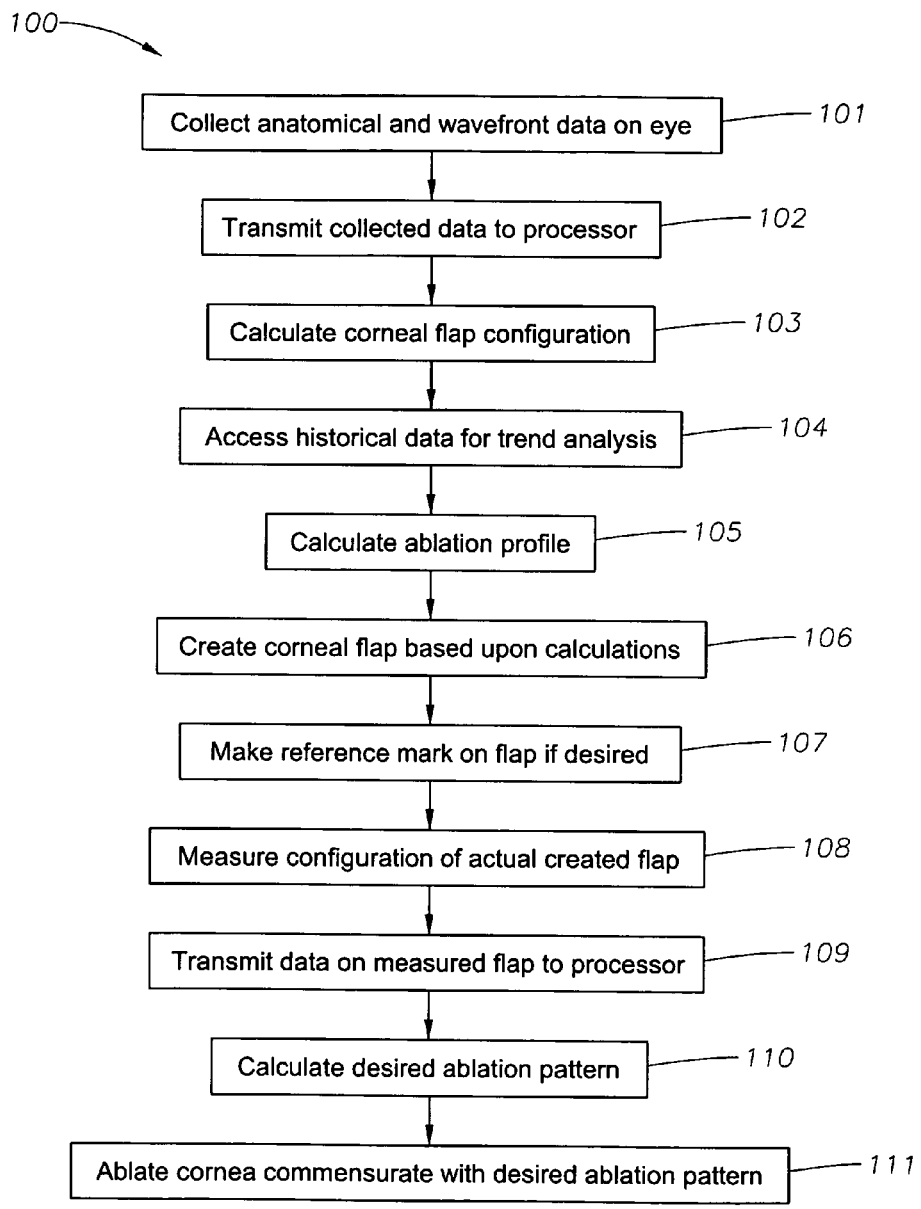

LASER CORNEAL FLAP CUTTING SYSTEM AND ASSOCIATED METHODS

CROSS-REFERENCE TO RELATED APPLICATIONS

This application claims priority under 35 U.S.C. §119 to U.S. Provisional Patent Application No. 60/703,671, filed Jul. 29, 2005, the entire contents of which are incorporated herein by reference.

TECHNICAL FIELD OF THE INVENTION

The present invention relates to systems and methods for performing laser-assisted corneal surgery, and, more particularly, to such systems and methods for integrating the cutting of a corneal flap with wavefront-guided refractive laser surgery.

BACKGROUND OF THE INVENTION

It is known in the art to perform corneal ablation by means of wavefront-guided refractive laser surgery. Typically a wavefront sensor measures an aberration map and its position relative to anatomical landmarks, which can be intrinsic or externally applied features. Aberration data, sometimes along with geometric registration information, can be transferred directly to a treatment excimer laser.

It is also known to use a femtosecond laser to cut a corneal flap prior to performing the corneal ablation. However, these procedures are not known to be coordinated, nor is a system known for optimizing the flap-cutting procedure within the limits of a flap-cutting device.

Therefore, it would be advantageous to provide a system and method for coordinating corneal ablation with the flap-cutting procedure and for optimizing same.

BRIEF SUMMARY OF THE INVENTION

The present invention is directed to a system and method for performing wavefront-guided laser surgery on a cornea. The method comprises the step of calculating a corneal flap configuration based upon collected anatomical information on an eye and wavefront data on a cornea of the eye. Such data may be collected by, for example, an aberrometer, although this is not intended as a limitation.

The calculated configuration is transmitted to a processor in controlling relation to a corneal flap-cutting device. The flap-cutting device is used to create a corneal flap based upon the calculated configuration.

A system for performing wavefront-guided laser surgery on a cornea comprises a processor and means for transmitting to the processor anatomical information collected on an eye and wavefront data collected on a cornea of the eye.

A software package is installable on the processor that is adapted to calculate a corneal flap configuration based upon the anatomical information and wavefront data. The corneal flap configuration can be an optimal flap configuration within the limits of the software package, the processor and the anatomical information and wavefront data provided to the processor, as well as based on any other predefined limits imposed by the software for a given application. The software package is also adapted to control a corneal flap-cutting device to cut a corneal flap commensurate with the calculated optimal corneal flap configuration.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE SEVERAL VIEWS OF THE DRAWINGS

A more complete understanding of the present invention and the advantages thereof may be acquired by referring to the following description, taken in conjunction with the accompanying drawings in which like reference numbers indicate like features and wherein:

FIG. 2 is a flowchart of an exemplary laser surgery method of the present invention.

DETAILED DESCRIPTION OF THE INVENTION

Figure 1:
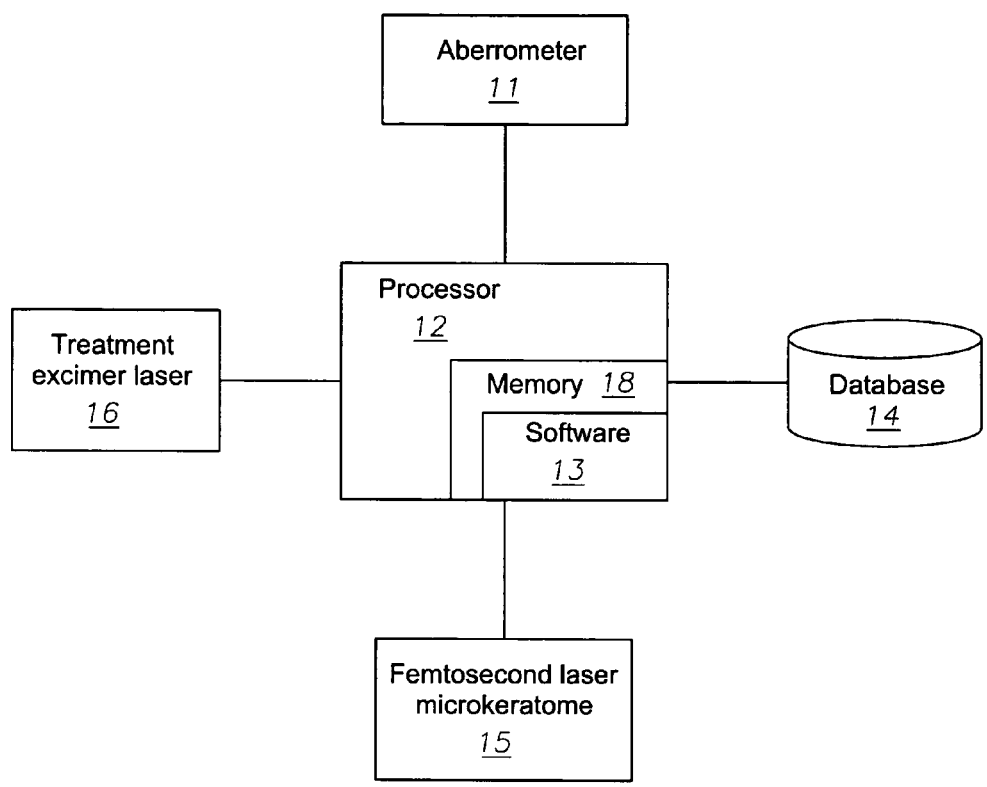
FIG. 1 is a schematic block diagram of a laser surgery system according to one embodiment of the present invention.

A description of the preferred embodiments of the present invention will now be presented with reference to FIGS. 1 and 2. An exemplary laser surgery system 10 is depicted schematically in FIG. 1, and an exemplary method 100, in FIG. 2.

The method 100 for performing wavefront-guided laser surgery on a cornea comprises the step of collecting anatomical information on an eye and wavefront data on a cornea using an aberrometer 11 (block 101). The collected anatomical information and wavefront data are transmitted to a processor 12 (block 102), which can comprise a memory 18 having a software package 13 installed thereon.

The software package 13 includes code segments for calculating a corneal flap configuration, which can be an optimal corneal flap configuration, based upon the collected anatomical information and wavefront data (block 103). The optimal flap configuration-may include, for example, an optimal flap geometry. A database 14 is accessible by the processor 12, the database 14 containing data on previously performed corneal laser surgery (block 104). The data may include data from prior cases for trend analysis, and may include changes in wavefront profiles along actual flap geometry, so that any consistent effects of specific flap creations on aberration profiles can be factored into future treatments. An optimal ablation profile can thus be calculated using the collected anatomical information, the wavefront data, and the accessed data (block 105).

The processor 12 is further in controlling relation to a corneal flap-cutting device, for example, a femtosecond laser microkeratome 15. The femtosecond laser microkeratome 15, under control of the software package 13 stored in memory 18, is used to create a corneal flap based upon the calculated configuration (block 106). A reference mark may also be made on the corneal flap during the flap-cutting step for use in tracking a corneal position during laser surgery (block 107). The created configuration of the corneal flap is then measured (block 108), since the actual flap created may differ from the ideal target flap configuration in position and/or shape. These measured data are transmitted to the processor 12 (block 109).

The, using the anatomical information, the wavefront data, and the corneal flap measured configuration, a laser ablation pattern is calculated (block 110), and a treatment laser 16, for example, an excimer laser, is controlled by the processor 12 and software package 13 to create the calculated laser ablation pattern (block 111).

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

What is claimed is:

1. A method for performing wavefront-guided laser surgery on a cornea comprising the steps of:
    calculating a corneal flap configuration based upon collected anatomical information on an eye and wavefront data on a cornea of the eye;
    transmitting the calculated corneal flap configuration to a processor in controlling relation to a femtosecond laser microkeratome;
    cutting a corneal flap based upon the calculated corneal flap configuration, wherein the cutting is performed by directing the femtosecond laser microkeratome onto the cornea;
    measuring a configuration of the created corneal flap;
    transmitting the measured configuration of the created corneal flap to the processor;
    calculating a laser ablation pattern using the anatomical information, the wavefront data, and the corneal flap measured configuration; and
    controlling a treatment laser to create the laser ablation pattern.

2. The method recited in claim 1, further comprising the step of collecting the anatomical information and the wavefront data using an aberrometer.

3. The method recited in claim 1, further comprising the step of calculating an ablation profile based upon the wavefront data of the cornea.

4. The method recited in claim 3, further comprising the step of accessing data on previously performed corneal laser surgery, and wherein the ablation-profile-calculating step is further based upon the accessed data.

5. The method recited in claim 3, wherein the corneal flap configuration calculating step comprises calculating a flap geometry.

6. The method recited in claim 1, further comprising the step of making a reference mark on the corneal flap during the cutting a corneal flap step for use in tracking a corneal position during laser surgery.

7. A system for performing wavefront-guided laser surgery on a cornea comprising:
    a processor;
    a memory;
    an aberrometer adapted to collect anatomical information on an eye and wavefront data on a cornea of the eye; and
    a software package installed on the memory and readable by the processor, the software package adapted to:
        receive the anatomical information and the wavefront data,
        calculate a corneal flap configuration based upon the anatomical information and wavefront data, and
        control a femtosecond laser microkeratome to cut a corneal flap commensurate with the calculated optimal corneal flap configuration;
    the aberrometer further adapted to measure a configuration of the created corneal flap;
    the software package further adapted to:
        calculate a laser ablation pattern using the anatomical information, the wavefront data, and the measured corneal flap configuration, and
        control a treatment laser to create the laser ablation pattern.

8. The system recited in claim 7, wherein the software package is further adapted to calculate an ablation profile based upon the wavefront measurement.

9. The system recited in claim 8, further comprising a database of data on previously performed corneal laser surgery, the database accessible by the processor, and wherein the software package is adapted to calculate the ablation profile based upon data accessed from the database.

10. The system recited in claim 7, wherein the software package is further adapted to control the femtosecond laser microkeratome to make a reference mark on the corneal flap for use in tracking a corneal position during laser surgery.

* * * * *